US008518893B2

(12) United States Patent
Minamitake et al.

(10) Patent No.: US 8,518,893 B2
(45) Date of Patent: Aug. 27, 2013

(54) MEDICAL COMPOSITIONS CONTAINING GHRELIN

(75) Inventors: Yoshiharu Minamitake, Gunma (JP); Masaru Matsumoto, Gunma (JP)

(73) Assignee: Asubio Pharma Co. Ltd., Tokyo (JP)

( * ) Notice: Subject to any disclaimer, the term of this patent is extended or adjusted under 35 U.S.C. 154(b) by 0 days.

(21) Appl. No.: 13/413,581

(22) Filed: Mar. 6, 2012

(65) Prior Publication Data

US 2012/0264691 A1  Oct. 18, 2012

Related U.S. Application Data

(60) Division of application No. 11/878,532, filed on Jul. 25, 2007, which is a continuation of application No. 10/500,561, filed as application No. PCT/JP03/06349 on May 21, 2003, now abandoned.

(30) Foreign Application Priority Data

May 21, 2002 (JP) .................................. 2002-146155

(51) Int. Cl.
*A61K 38/16* (2006.01)
*A61K 49/14* (2006.01)

(52) U.S. Cl.
USPC ............................ 514/21.3; 530/324; 424/9.2

(58) Field of Classification Search
None
See application file for complete search history.

(56) References Cited

U.S. PATENT DOCUMENTS

| 4,897,470 | A |   | 1/1990  | Yoshimoto et al. |         |
|-----------|---|---|---------|------------------|---------|
| 5,503,827 | A |   | 4/1996  | Woog et al.      |         |
| 5,843,903 | A | * | 12/1998 | Schally et al.   | 514/19.3|
| 5,998,381 | A | * | 12/1999 | Shekhani et al.  | 514/25  |
| 6,967,237 | B2|   | 11/2005 | Bednarek         |         |
| 7,385,026 | B1| * | 6/2008  | Kangawa et al.   | 530/324 |

FOREIGN PATENT DOCUMENTS

| EP | 199992       |   | 11/1986 |
|----|--------------|---|---------|
| EP | 1197496 A1   |   | 4/2002  |
| JP | 61221125     |   | 11/1986 |
| JP | 02096533     |   | 4/1990  |
| WO | WO 9501185   |   | 1/1995  |
| WO | WO-01/07475  | * | 2/2001  |
| WO | WO 0187335   |   | 11/2001 |
| WO | WO 0192292 A2|   | 12/2001 |

OTHER PUBLICATIONS

From Website: http://www.sciencelab.com/msds.php?msdsId=9925514, Material Safety Data Sheet 1% AcOH, last update: Nov. 1, 2010, 6 pages.*
Kaiya, 2001, The Journal of Biological Chemistry, 276, 40441-40448, cited on the IDS dated Mar. 6, 2012.*
Pace, 1996, FASEB, J., 10, 75-83.*
Website: www.piercenet.com, 2 pages, latest update Sep. 2005.*
[Retrieved from]: http://en.allexperts.com/q/Chemicals-2460/Destrose-Saline.htm, 2009, 2 pages [Retrieved on Dec. 28, 2009].
[Retrieved from]: http://www.answers.com/topic/saline-solution-1, 2009, 2 pages [Retrieved on Mar. 25, 2009].
[Retrieved from]: http://www.britannica.com/EBchecked/topic/504086/Ringers-solution, 2009, 2 pages [Retrieved on Mar. 25, 2009].
[Retrieved from]: http://wiki.answers.com/Q/What_is_the_LD50_of_methanol_for_a_100_gram_rat, [retrieved on Jul. 17, 2011].
[Retrieved from]: http://www.apple-cider-vinegar-benefits.com/properties-of-vinegar.html, 4 pages, 2010, [retrieved on Sep. 6, 2010].
[Retrieved from]: http://www.midi-inc.com/pdf/MSDS_Methanol.pdf, 6 pages, [retrieved on Jul. 16, 2011].
"wikianswers.com-pH of physiological saline?" (Oct. 14, 2009).
"www.answers.com-saline" (Oct. 14, 2009).
"www.britannica.com-saline" (Oct. 14, 2009).
Arvat E. et al., "Endocrine activities of ghrelin, a natural growth hormone secretagogue (GHS), in humans: comparison and interactions with hexarelin, a nonnatural peptidyl GHS, and GH-releasing hormone," Journal of Clinical Endocrinology and Metabolism, Mar. 2001, vol. 86(3), p. 1169-74, ISSN: 0021-972X.
Eckert Animal Physiology: Mechanisms and Adaptations (1997) pp. 532-535, Figure 13-18.
Elipe, et al., H NMR Structural Analysis of Human Ghrelin and Its Six Truncated Analogs, Biopolymers, vol. 59, pp. 489-501 (2001).
Hosoda, et al; Purification and Characterization of Rat des-Gin[14] Ghrelin, a Second Endogenous Ligand for the Growth Hormone Secretagogue Receptor, The Journal of Biological Chemistry; vol. 275, No. 29, Issue of Jul. 21, pp. 21995-22200, 2000.
Isimaru, Masanori et al., "Stability of the octanoyl group essential for expressing the biological activities of rat ghrelin," Peptide Science 2002, Mar. 2003, 157-160, ISSN: 1344-7661.
Kaiya, 2001, The Journal of Biological Chemistry, 276, 40441-40448.
Kanamoto, et al (2001) The Journal of Clinical Endocrinology & Metabolism 88(10): 4984-4990.
Matsumoto, et al., Biochemical and biophysical Research communications, 2001, 287, 142-146.
PCT/ISN220 and PCT/ISN210 dated Jul. 22, 2003.
Peino R. et al., "Ghrelin-induced growth hormone secretion in humans," European Journal of Endocrinology, Nov. 2000, vol. 143(5), r11-14, ISSN: 0804-4643.

(Continued)

*Primary Examiner* — Satyanarayana R Gudibande
(74) *Attorney, Agent, or Firm* — Hunton & Williams LLP

(57) ABSTRACT

It is provided a pharmaceutical composition stably containing ghrelin or its derivative, which is an endogenous growth hormone secretagogue (GHS) to a growth hormone secretagogue-receptor (GHS-R), comprising a aqueous solution containing the ghrelins having pH range of 2 to 7, wherein the aqueous solution having pH range of 2 to 7 is a buffer solution, especially, glycine hydrochloride buffer, acetate buffer, citrate buffer, lactate buffer, phosphate buffer, citric acid-phosphate buffer, phosphate-acetate-borate buffer or phthalate buffer, and the concentration of the ghrelins in the solution is from 0.03 nmol/mL to 6 μmol/mL.

11 Claims, 3 Drawing Sheets

(56) References Cited

OTHER PUBLICATIONS

Seoane L.M. et at., "Ghrelin elicits a marked stimulatory effect on GH secretion in freelymoving rats," European Journal of Endocrinology, Nov. 2000, vol. 143(5), R7-9, ISSN: 0804-4643.
Sugino, 2002, BBRC, 295, 255-260.
The Alliance for Cellular Signaling (AfCS) Ringer's Solution Protocol (Oct. 14, 2009) www.signaling-gateway.org.
Voet, et al., Biochemistry, 1995, II Edition, John Wiley & Sons, Inc., pp. 60-62 and 77.
Wren, 2001, Diabetes, 50, 2540-2547.
Hosoda, et al. (2004) Clinical Chemistry 50 (6): 1077-1080.

* cited by examiner

```
SEQUENCE LISTING

<160> NUMBER OF SEQ ID NOS: 21

<210> SEQ ID NO 1
<211> LENGTH: 28
<212> TYPE: PRT
<213> ORGANISM: Homo sapiens
<220> FEATURE:
<221> NAME/KEY: PEPTIDE
<222> LOCATION: (1)..(28)
<223> OTHER INFORMATION: Amino acid sequence for human endogenous
      peptides of growth hormone secretagogue

<400> SEQUENCE: 1

Gly Ser Ser Phe Leu Ser Pro Glu His Gln Arg Val Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 27
<212> TYPE: PRT
<213> ORGANISM: Homo sapiens
```

```
<220> FEATURE:
<221> NAME/KEY: PEPTIDE
<222> LOCATION: (1)..(27)
<223> OTHER INFORMATION: Amino acid sequence for human endogenous
      peptides (27 amino acids) of growth hormone secretagogue

<400> SEQUENCE: 2

Gly Ser Ser Phe Leu Ser Pro Glu His Gln Arg Val Gln Arg Lys Glu
1               5                   10                  15

Ser Lys Lys Pro Pro Ala Lys Leu Gln Pro Arg
            20                  25

<210> SEQ ID NO 3
<211> LENGTH: 28
<212> TYPE: PRT
<213> ORGANISM: Rattus norvegicus
<220> FEATURE:
<221> NAME/KEY: PEPTIDE
<222> LOCATION: (1)..(28)
<223> OTHER INFORMATION: Amino acid sequence for rat endogenous peptides
      of growth hormone secretagogue

<400> SEQUENCE: 3

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 4
<211> LENGTH: 27
<212> TYPE: PRT
<213> ORGANISM: Rattus norvegicus
<220> FEATURE:
<221> NAME/KEY: PEPTIDE
<222> LOCATION: (1)..(27)
<223> OTHER INFORMATION: Amiino acid sequence for rat endogenous
      peptides of growth hormone secretagogue

<400> SEQUENCE: 4

Gly Ser Ser Phe Leu Ser Pro Glu His Gln Lys Ala Gln Arg Lys Glu
1               5                   10                  15

Ser Lys Lys Pro Pro Ala Lys Leu Gln Pro Arg
            20                  25

<210> SEQ ID NO 5
<211> LENGTH: 28
<212> TYPE: PRT
<213> ORGANISM: Mus musculus
<220> FEATURE:
<221> NAME/KEY: PEPTIDE
<222> LOCATION: (1)..(28)
<223> OTHER INFORMATION: Amino acid sequence for mouse endogenous
      peptides of growth hormone secretagogue

<400> SEQUENCE: 5

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 6
<211> LENGTH: 28
<212> TYPE: PRT
<213> ORGANISM: Sus scrofa
<220> FEATURE:
<221> NAME/KEY: PEPTIDE
<222> LOCATION: (1)..(28)
<223> OTHER INFORMATION: Amino acid sequence for porcine endogenous
``` peptides of growth hormone secretagogue

<400> SEQUENCE: 6

Gly Ser Ser Phe Leu Ser Pro Glu His Gln Lys Val Gln Gln Arg Lys
1               5                   10                  15

Glu Ser Lys Lys Pro Ala Ala Lys Leu Lys Pro Arg
            20                  25

<210> SEQ ID NO 7
<211> LENGTH: 27
<212> TYPE: PRT
<213> ORGANISM: Bos taurus
<220> FEATURE:
<221> NAME/KEY: PEPTIDE
<222> LOCATION: (1)..(27)
<223> OTHER INFORMATION: Amino acid sequence for bovine endogenous
      peptides (27 amino acids) of growth hormone secretagogue

<400> SEQUENCE: 7

Gly Ser Ser Phe Leu Ser Pro Glu His Gln Lys Leu Gln Arg Lys Glu
1               5                   10                  15

Ala Lys Lys Pro Ser Gly Arg Leu Lys Pro Arg
            20                  25

<210> SEQ ID NO 8
<211> LENGTH: 27
<212> TYPE: PRT
<213> ORGANISM: Ovis aries
<220> FEATURE:
<221> NAME/KEY: PEPTIDE
<222> LOCATION: (1)..(27)
<223> OTHER INFORMATION: Amino acid sequence for ovine endogenous
      peptides (27 amino acids) of growth hormone secretagogue

<400> SEQUENCE: 8

Gly Ser Ser Phe Leu Ser Pro Glu His Gln Lys Leu Gln Arg Lys Glu
1               5                   10                  15

Pro Lys Lys Pro Ser Gly Arg Leu Lys Pro Arg
            20                  25

<210> SEQ ID NO 9
<211> LENGTH: 28
<212> TYPE: PRT
<213> ORGANISM: Canis familiaris
<220> FEATURE:
<221> NAME/KEY: PEPTIDE
<222> LOCATION: (1)..(28)
<223> OTHER INFORMATION: Amino acid sequence for dog endogenous peptides
      of growth hormone secretagogue

<400> SEQUENCE: 9

Gly Ser Ser Phe Leu Ser Pro Glu His Gln Lys Leu Gln Gln Arg Lys
1               5                   10                  15

Glu Ser Lys Lys Pro Pro Ala Lys Leu Gln Pro Arg
            20                  25

<210> SEQ ID NO 10
<211> LENGTH: 21
<212> TYPE: PRT
<213> ORGANISM: Anguilla japonica
<220> FEATURE:
<221> NAME/KEY: PEPTIDE
<222> LOCATION: (1)..(21)
<223> OTHER INFORMATION: Amino acid sequence for eel endogenous peptides
      of growth hormone secretagogue. This peptide is amidated at C-
      terminus.

<400> SEQUENCE: 10

-continued

Gly Ser Ser Phe Leu Ser Pro Ser Gln Arg Pro Gln Gly Lys Asp Lys
1               5                   10                  15

Lys Pro Pro Arg Val
            20

<210> SEQ ID NO 11
<211> LENGTH: 23
<212> TYPE: PRT
<213> ORGANISM: Oncorhynchus mykiss
<220> FEATURE:
<221> NAME/KEY: PEPTIDE
<222> LOCATION: (1)..(23)
<223> OTHER INFORMATION: Amino acid sequence for rainbow trout
      endogenous peptides (23 amino acids) of growth hormone
      secretagogue. This peptide is amidated at C-terminus.

<400> SEQUENCE: 11

Gly Ser Ser Phe Leu Ser Pro Ser Gln Lys Pro Gln Val Arg Gln Gly
1               5                   10                  15

Lys Gly Lys Pro Pro Arg Val
            20

<210> SEQ ID NO 12
<211> LENGTH: 20
<212> TYPE: PRT
<213> ORGANISM: Oncorhynchus mykiss
<220> FEATURE:
<221> NAME/KEY: PEPTIDE
<222> LOCATION: (1)..(20)
<223> OTHER INFORMATION: Amino acid sequence for rainbow trout
      endogenous peptides (20 amino acids) of growth hormone
      secretagogue.  This peptide is amidated at C-terminus.

<400> SEQUENCE: 12

Gly Ser Ser Phe Leu Ser Pro Ser Gln Lys Pro Gln Gly Lys Gly Lys
1               5                   10                  15

Pro Pro Arg Val
            20

<210> SEQ ID NO 13
<211> LENGTH: 24
<212> TYPE: PRT
<213> ORGANISM: Gallus domesticus
<220> FEATURE:
<221> NAME/KEY: PEPTIDE
<222> LOCATION: (1)..(24)
<223> OTHER INFORMATION: Amino acid sequence for chicken endogenous
      peptides of growth hormone secretagogue

<400> SEQUENCE: 13

Gly Ser Ser Phe Leu Ser Pro Thr Tyr Lys Asn Ile Gln Gln Gln Lys
1               5                   10                  15

Gly Thr Arg Lys Pro Thr Ala Arg
            20

<210> SEQ ID NO 14
<211> LENGTH: 24
<212> TYPE: PRT
<213> ORGANISM: Gallus domesticus
<220> FEATURE:
<221> NAME/KEY: PEPTIDE
<222> LOCATION: (1)..(24)
<223> OTHER INFORMATION: Amino acid sequence for chicken endogenous
      peptides of growth hormone secretagogue

<400> SEQUENCE: 14

Gly Ser Ser Phe Leu Ser Pro Thr Tyr Lys Asn Ile Gln Gln Gln Lys

```
                1               5                  10                 15
Asp Thr Arg Lys Pro Thr Ala Arg
                20

<210> SEQ ID NO 15
<211> LENGTH: 26
<212> TYPE: PRT
<213> ORGANISM: Gallus domesticus
<220> FEATURE:
<221> NAME/KEY: PEPTIDE
<222> LOCATION: (1)..(26)
<223> OTHER INFORMATION: Amino acid sequence for chicken endogenous
      peptides of growth hormone secretagogue

<400> SEQUENCE: 15

Gly Ser Ser Phe Leu Ser Pro Thr Tyr Lys Asn Ile Gln Gln Gln Lys
1               5                   10                  15

Asp Thr Arg Lys Pro Thr Ala Arg Leu His
                20                  25

<210> SEQ ID NO 16
<211> LENGTH: 27
<212> TYPE: PRT
<213> ORGANISM: Rana catesbeiana
<220> FEATURE:
<221> NAME/KEY: PEPTIDE
<222> LOCATION: (1)..(27)
<223> OTHER INFORMATION: Amino acid sequence for frog endogenous
      peptides of growth hormone secretagogue

<400> SEQUENCE: 16

Gly Leu Thr Phe Leu Ser Pro Ala Asp Met Gln Lys Ile Ala Glu Arg
1               5                   10                  15

Gln Ser Gln Asn Lys Leu Arg His Gly Asn Met
                20                  25

<210> SEQ ID NO 17
<211> LENGTH: 28
<212> TYPE: PRT
<213> ORGANISM: Rana catesbeiana
<220> FEATURE:
<221> NAME/KEY: PEPTIDE
<222> LOCATION: (1)..(28)
<223> OTHER INFORMATION: Amino acid sequence for frog endogenous
      peptides of growth hormone secretagogue

<400> SEQUENCE: 17

Gly Leu Thr Phe Leu Ser Pro Ala Asp Met Gln Lys Ile Ala Glu Arg
1               5                   10                  15

Gln Ser Gln Asn Lys Leu Arg His Gly Asn Met Asn
                20                  25

<210> SEQ ID NO 18
<211> LENGTH: 20
<212> TYPE: PRT
<213> ORGANISM: Tilapia nilotica
<220> FEATURE:
<221> NAME/KEY: PEPTIDE
<222> LOCATION: (1)..(20)
<223> OTHER INFORMATION: Amino acid sequence for tilapia endogenous
      peptides of growth hormone secretagogue.  Amidation

<400> SEQUENCE: 18

Gly Ser Ser Phe Leu Ser Pro Ser Gln Lys Pro Gln Asn Lys Val Lys
1               5                   10                  15

Ser Ser Arg Ile
                20
```

```
<210> SEQ ID NO 19
<211> LENGTH: 22
<212> TYPE: PRT
<213> ORGANISM: Silurus asotus
<220> FEATURE:
<221> NAME/KEY: PEPTIDE
<222> LOCATION: (1)..(22)
<223> OTHER INFORMATION: Amino acid sequence for catfish endogenous
      peptides of growth hormone secretagogue.  This peptide is
      amidated at C-terminus.

<400> SEQUENCE: 19

Gly Ser Ser Phe Leu Ser Pro Thr Gln Lys Pro Gln Asn Arg Gly Asp
1               5                   10                  15

Arg Lys Pro Pro Arg Val
            20

<210> SEQ ID NO 20
<211> LENGTH: 23
<212> TYPE: PRT
<213> ORGANISM: Silurus asotus
<220> FEATURE:
<221> NAME/KEY: PEPTIDE
<222> LOCATION: (1)..(23)
<223> OTHER INFORMATION: Amino acid sequence for catfish endogenous
      peptides of growth hormone secretagogue

<400> SEQUENCE: 20

Gly Ser Ser Phe Leu Ser Pro Thr Gln Lys Pro Gln Asn Arg Gly Asp
1               5                   10                  15

Arg Lys Pro Pro Arg Val Gly
            20

<210> SEQ ID NO 21
<211> LENGTH: 28
<212> TYPE: PRT
<213> ORGANISM: Equus caballus
<220> FEATURE:
<221> NAME/KEY: PEPTIDE
<222> LOCATION: (1)..(28)
<223> OTHER INFORMATION: Amino acid sequence for equine endogenous
      peptides of growth hormone secretagogue

<400> SEQUENCE: 21

Gly Ser Ser Phe Leu Ser Pro Glu His His Lys Val Gln His Arg Lys
1               5                   10                  15

Glu Ser Lys Lys Pro Pro Ala Lys Leu Lys Pro Arg
            20                  25
```

MEDICAL COMPOSITIONS CONTAINING GHRELIN

CROSS-REFERENCE TO RELATED APPLICATIONS

This application is a divisional of U.S. patent application Ser. No. 11/878,532, filed Jul. 25, 2007, which is a continuation of U.S. patent application Ser. No. 10/500,561, filed Mar. 21, 2005 now abandoned, which is the U.S. National Phase of International Application No. PCT/JP03/06349 filed on May 21, 2003, which claims priority to Japanese Application No. JP 2002-146155 filed May 21, 2002, all of which are incorporated herein by reference in their entireties.

TECHNICAL FIELD

The present invention relates to a pharmaceutical composition containing ghrelin or derivative thereof, which is an endogenous growth hormone secretagogue (GHS) to a growth hormone secretagogue-receptor (GHS-R) in a stable state, as well as to a method for preventing degradation of modifying hydrophobic group of ghrelin or its derivative in an aqueous solution dissolved ghrelin or its derivative therein.

BACKGROUND ART

Ghrelin, an endogenous growth hormone secretagogue (GHS) to growth hormone secretagogue receptor (GHS-R) which is one of orphan receptors, is a physiologically active peptide first isolated and purified from rat in 1999 (Kojima, et al., *Nature*, 402: 656-660, 1999). Thereafter, some ghrelins having same chemical structure of rat ghrelin have been isolated from vertebrates other than rat, such as human, mouse, pig, chicken, eel, bovine, equine, ovine, frog, trout and canine. The chemical structures of these ghrelins are listed in the following Table 1.

TABLE 1

| | |
|---|---|
| Human | GSS(n-octanoyl)FLSPEHQRVQQRKESKKPPAKLQPR |
| | GSS(n-octanoyl)FLSPEHQRVQRKESKKPPAKLQPR |
| Rat | GSS(n-octanoyl)FLSPEHQKAQQRKESKKPPAKLQPR |
| | GSS(n-octanoyl)FLSPEHQKAQRKESKKPPAKLQPR |
| Mouse | GSS(n-octanoyl)FLSPEHQKAQQRKESKKPPAKLQPR |
| Porcine | GSS(n-octanoyl)FLSPEHQKVQQRKESKKPAAKLKPR |
| Bovine | GSS(n-octanoyl)FLSPEHQKLQRKEAKKPSGRLKPR |
| Ovine | GSS(n-octanoyl)FLSPEHQKLQRKEPKKPSGRLKPR |
| Canine | GSS(n-octanoyl)FLSPEHQKLQQRKESKKPPAKLQPR |
| Eel | GSS(n-octanoyl)FLSPSQRPQGKDKKPPRV-NH$_2$ |
| Trout | GSS(n-octanoyl)FLSPSQKPQVRQGKGKPPRV-NH$_2$ |
| | GSS(n-octanoyl)FLSPSQKPQGKGKPPRV-NH$_2$ |
| Chicken | GSS(n-octanoyl)FLSPTYKNIQQQKGTRKPTAR |
| | GSS(n-octanoyl)FLSPTYKNIQQQKDTRKPTAR |
| | GSS(n-octanoyl)FLSPTYKNIQQQKDTRKPTARLH |
| Bullfrog | GLT(n-octanoyl)FLSPADMQKIAERQSQNKLRHGNM |
| | GLT(n-decanoyl)FLSPADMQKIAERQSQNKLRHGNM |
| | GLT(n-octanoyl)FLSPADMQKIAERQSQNKLRHGNMN |
| Tilapia | GSS(n-octanoyl)FLSPSQKPQNKVKSSRI-NH$_2$ |
| Catfish | GSS(n-octanoyl)FLSPTQKPQNRGDRKPPRV-NH$_2$ |
| | GSS(n-octanoyl)FLSPTQKPQNRGDRKPPRVG |
| Equine | GSS(n-butanoyl)FLSPEHHKVQHRKESKKPPAKLKPR |

(wherein, an amino acid residue is written by the one letter notation defined by IUPAC and IUC)

These peptides are characterized by a specific structure due to acylation of hydroxyl group at the side chain of serine group (S) or threonine group (T) by fatty acid such as octanoic acid or decanoic acid, and there has never been isolated the physiologically active peptides having modifying hydrophobic group such as ghrelin. These new peptides exhibit potent promoting effect for secretion of growth hormone, and it has become clear that these peptides perform for adjusting the secretion of growth hormone. Therefore, many researchers have great interest in physiologically active roll of ghrelin and for development of these peptides as medicines (e.g., World Patent Publication WO 01/07475).

It is known that the modifying hydrophobic group in ghrelin molecule has to be necessary for exhibiting the physiological effects (Kojima, et al., *Nature*, 402; 656-660, 1999). However, due to the non-existence of peptides like ghrelin having the modifying hydrophobic group in molecule at the hydroxyl group of side chain of specific amino acid residue, the stability of these peptides for development as medicines have never been studied.

Incidentally, the compound to be developed as medicines has the various kinds of chemical structures, and because of these chemical structures, the compounds may easily degrade in the formulation process or in the storage process thereafter. The degradation reactions are hydrolytic cleavage, dehydration, isomerization, oxidization, reduction or photodegradation of the compound, and further, the chemical reaction of the compound with additives to be formulated with the compound. Therefore, it is very important to study and understand the varieties of the degradation reaction and the degrees thereof from the chemical structure of the compounds, for development of the compound as medicines, and consequence quality control thereof.

It is well known that the stability of medicines may be greatly controlled by the ambient environmental condition, such as pH level of the environment. The influence of pH of the solution for the degradation rate of medicines in aqueous state has been studied, and pH profile of degradation rate of many medicines has been reported (e.g., Sumie Yoshioka, "*Stability of Medicines*" by Nankohdo, 1995).

The physiologically active peptides or physiologically active proteins are inactivated and degraded by protease existing in the digestive organ, and it is difficult to develop the oral administrable composition containing these peptides or proteins. Therefore, these peptides or proteins are prepared as an injectable composition for the clinical administration, and for this purpose the stability of these substances in the aqueous solution is very important for preparation of the liquid pharmaceutical formulations regardless of the dosage form such as solution form or soluble solution form in site.

At present, pharmaceutical compositions containing various kinds of peptide or protein such as insulin, growth hormone, calcitonin, atrial natriuretic peptide, LH-RH (luteinizing hormone-releasing hormone) derivatives or adrenocorticotropic hormone derivatives are on sale as medicines, and it is reported that the chemical changes of these peptides or proteins are deamidation, iso-aspartic acid formation, hydrolytic cleavage such as fragmentation, racemization, formation of disulfide bond or exchange reaction, β-elimination or oxidative reaction.

These chemical changes exert an influence on the stability of the composition containing peptides or proteins, and the degrees of the degradation reaction of peptides or proteins is dependent on a pH value of the solution. For example, it is reported that the chemical structure of degradation products and the produced amount of the degradation products varied according to the pH value of the solution containing these peptides or proteins, such as LH-RH derivatives (Strickley et al., *Pharm. Res.*, 7, 530-536, 1990), human parathyroid hormone (Nobuchi et al., *Pharm. Res.*, 14, 1685-1690, 1997) hirudin (antithrombin substance: Gietz et al., *Pharm. Res.*, 15, 1456-1462, 1998), and human amylin derivatives (Hekmann et al., *Pharm. Res.*, 15, 650-659 1998).

Ghrelin or its derivative of the present invention is a physiologically active peptide, and it is common to prepare an aqueous solution containing ghrelin as pharmaceutical composition for medicine. Though the stability of ghrelin in the aqueous solution is very important for preparation of the pharmaceutical composition, there has never been any study of the stability of ghrelin in the aqueous solution. Ghrelin or its derivative has the specific modifying hydrophobic group in its molecule, that is, the side chained hydroxyl group of certain amino acid residue of ghrelin or its derivative is acylated by fatty acid. There has never been discovered a peptide like ghrelin having the specific modifying hydrophobic group in molecule, therefore, the common knowledge about the stability of ghrelin has also never been reported. That is, it is unknown about the stability, the chemical structure of degradation product and the mechanism of production of the degradation product of ghrelin. Further, it is unknown about the mechanism of degradation of modifying hydrophobic group of ghrelin, as well as the secondary degradation from the degradation product of ghrelin.

Under these circumstances, the objective of the present invention is to provide a pharmaceutical composition stably containing ghrelin or its derivative and a method for preventing degradation of modifying hydrophobic group of ghrelin or its derivative in an aqueous solution dissolved ghrelin or its derivative therein based on the knowledge obtained by the investigation of the chemical stability of ghrelin or its derivative having specific modifying hydrophobic group in the molecule.

Through extensive investigations of the influence of pH in an aqueous solution containing ghrelin and the chemical structure of the degradation product from ghrelin, the present inventors discovered that, in an aqueous solution, ghrelin degraded to produce desacyl compound by hydrolytic cleavage of the specific modifying hydrophobic group and in addition, degraded to produce dehydroalanine compound by β-elimination of modifying hydrophobic group, consequently to produce the secondary degradation product due to the volatility of dehydroalanine compound, and these degradation were affected by pH value of the aqueous solution.

Based on the results of the mechanism of degradation of ghrelin mentioned above, the present inventors further discovered that the pharmaceutical composition stably containing ghrelin could be obtained by adjusting pH of the solution with pH adjuster or buffer agent, and this stabilization effect could be obtained by various sorts of the buffer agent independent of their concentration or ghrelin concentration, and thus completed the present invention.

DISCLOSURE OF INVENTION

Accordingly, as one aspect of the present invention, it is provided a pharmaceutical aqueous composition containing ghrelin or its derivative (herein after and in claims referred to as "the ghrelins"), wherein pH of an aqueous solution dissolving the ghrelins is from 2 to 7.

More specifically, the present invention provides the following:
(1) A pharmaceutical composition containing the ghrelins, wherein pH of an aqueous solution dissolving the ghrelins is from 2 to 7.
(2) A pharmaceutical composition according to (1), wherein said pH is from 3 to 6.
(3) A pharmaceutical composition according to (1) or (2), in which a pH adjuster or a buffer agent is further contained.
(4) A pharmaceutical composition according to (3), wherein the pH adjuster is one or more selected from the group consisting of hydrochloric acid, sulfuric acid, nitric acid, boric acid, carbonic acid, bicarbonic acid, gluconic acid, sodium hydroxide, potassium hydroxide, aqueous ammonia, citric acid, monoethanolamine, lactic acid, acetic acid, succinic acid, fumaric acid, maleic acid, phosphoric acid, methanesulfonic acid, malic acid, propionic acid, trifluoroacetic acid and salt thereof.
(5) A pharmaceutical composition according to (3), wherein the buffer agent is one or more selected from the group consisting of glycine, acetic acid, citric acid, boric acid, phthalic acid, phosphoric acid, succinic acid, lactic acid, tartaric acid, carbonic acid, hydrochloric acid, sodium hydroxide and the salt thereof.
(6) A pharmaceutical composition according to any one of (3) to (5), wherein concentration of the pH adjuster or the buffer agent in the solution is in the range of from 0.01 mM to 1000 mM.
(7) A pharmaceutical composition according to any one of (1) to (6), wherein the solution is buffer solution.
(8) A pharmaceutical composition according to (7), wherein the buffer solution is glycine hydrochloride buffer, acetate buffer, citrate buffer, lactate buffer, phosphate buffer, citric acid-phosphate buffer, phosphate-acetate-borate buffer or phthalate buffer.
(9) A pharmaceutical composition according to any one of (1) to (8), wherein the concentration of the ghrelins in the solution is in the range of 0.03 nmol/mL to 6 μmol/mL.
(10) A pharmaceutical composition according to any one of (1) to (9), wherein the ghrelins is acetic acid salt.
(11) A pharmaceutical composition according to any one of (1) to (10), wherein the ghrelins is human ghrelin.
(12) A pharmaceutical composition according to any one of (1) to (11), wherein an anti-adsorbent is further contained.
(13) A pharmaceutical composition according to (12), wherein the concentration of the anti-adsorbent is in the range of from 0.001% to 5%.
(14) A pharmaceutical composition according to (12) or (13), wherein the anti-adsorbent is surfactant.
(15) A pharmaceutical composition containing the ghrelins, in which powder obtained from a solution of any one of (1) to (14) by drying is contained.
(16) A pharmaceutical composition according to (15), wherein the powder is a lyophilized powder.
(17) A method for preventing a degradation of hydrophobic group of the ghrelins in a solution containing the ghrelins which comprises adjusting pH of the solution in the range of 2 to 7.
(18) A method according to (17), wherein said pH of the solution is adjusted to 3 to 6.
(19) A method according to (17) or (18), wherein a pH adjuster or a buffer agent is further contained.
(20) A method according to (19), wherein one or more pH adjuster selected from the group consisting of hydrochloric acid, sulfuric acid, nitric acid, boric acid, carbonic acid, bicarbonic acid, gluconic acid, sodium hydroxide, potassium hydroxide, aqueous ammonia, citric acid, monoethanolamine, lactic acid, acetic acid, succinic acid, fumaric acid, maleic acid, phosphoric acid, methanesulfonic acid, malic acid, propionic acid, trifluoroacetic acid and salt thereof is contained.
(21) A method according to (19), wherein one or more buffer agent selected from the group consisting of glycine, acetic acid, citric acid, boric acid, phthalic acid, phosphoric acid, succinic acid, lactic acid, tartaric acid, carbonic acid, hydrochloric acid, sodium hydroxide and the salt thereof is contained.

(22) A method according to any one of (19) to (21), wherein concentration of the pH adjuster or the buffer agent in the solution is in the range of 0.01 mM to 1000 mM.
(23) A method according to any one of (17) to (22), wherein the solution is buffer solution.
(24) A method according to (23), wherein the buffer solution is glycine hydrochloride buffer, acetate buffer, citrate buffer, lactate buffer, phosphate buffer, citric acid-phosphate buffer, phosphate-acetate-borate buffer or phthalate buffer.
(25) A method according to any one of (17) to (24), wherein the concentration of the ghrelins in the solution is in the range of 0.03 nmol/mL to 6 µmol/mL.
(26) A method according to any one of (17) to (25), wherein the ghrelins is acetic acid salt.
(27) A method according to any one of (17) to (26), wherein the ghrelins is human ghrelin.

BEST MODE FOR CARRYING OUT THE INVENTION

Figure 1:
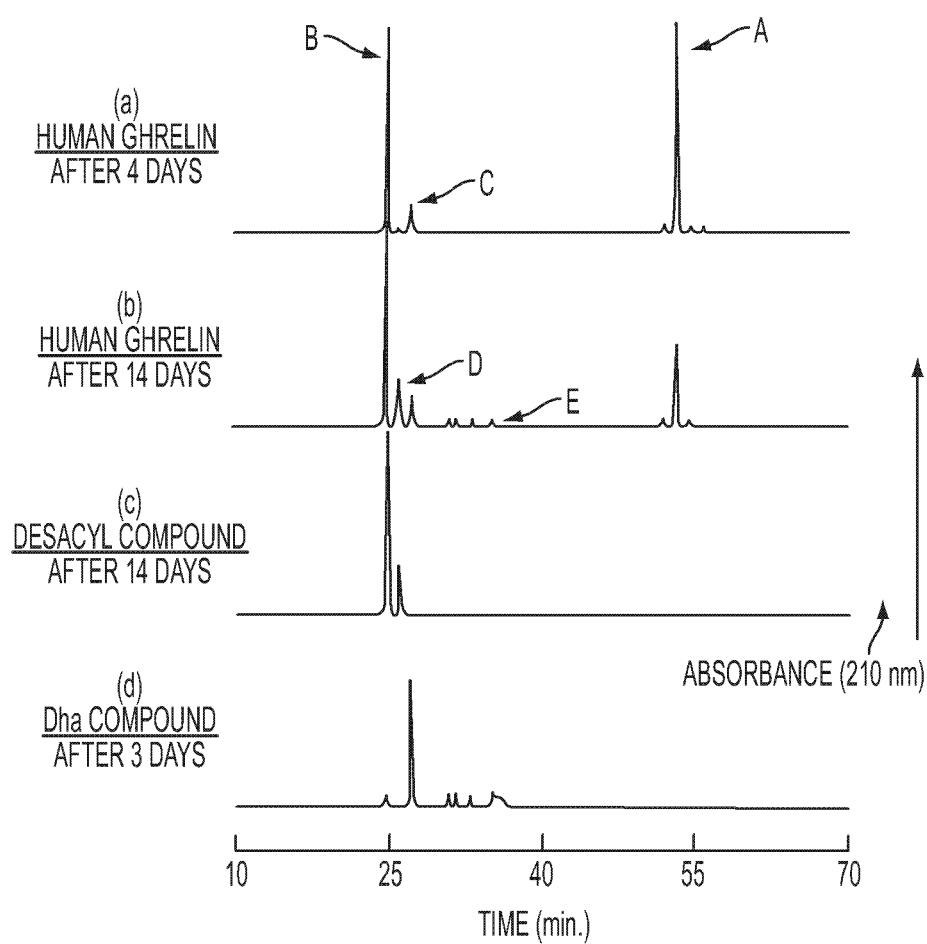
FIG. 1 shows the HPLC chart regarding the degradation patterns of desacyl compound and Dha compound in an aqueous solution of the ghrelins in Example 1.

The pharmaceutical composition of the present invention will now be explained more specifically as following.
The ghrelins to be used in the present invention are endogenous growth hormone secretagogues, which are peptides having effect of increasing the intracellular calcium ion concentration and inducing the secretion of growth hormone. The suitable ghrelins are those obtained from human, rat, porcine, chicken, eel, bovine, equine, ovine, frog, trout or canine. In the present invention, the ghrelins obtained from human is preferably used, and more preferably, human ghrelin obtained from human and having 28 amino acid residues is used.
The modifying hydrophobic group, which is a characteristic of the ghrelins, is not limited to octanoyl ($C_8$) group, and is a residue of fatty acid having 2 to 20, preferably 4 to 12 carbon atoms, such as hexanoyl ($C_6$) group, decanoyl ($C_{10}$) group or dodecanoyl ($C_{12}$) group. Further, the hydrophobic group is a residue of branched, saturated or unsaturated fatty acid, a residue of fatty acid having an aromatic group such as phenylpropionyl group, and an adamantane skeleton.
Therefore, the ghrelin derivatives of the present invention include the peptides listed in the above-mentioned Table 1, in which the amino acid sequence is modified by the insertion, addition and deletion of one or more amino acid, and/or the substitution by other amino acid to said amino acid sequence, and is modified chemically if necessary. Further, the ghrelin derivatives of the present, invention include the peptides in which modifying hydrophobic group is bonded to amino acid chain by ester bond and having same physiologically activity as the ghrelins.
The ghrelins to be used in the pharmaceutical composition of the present invention include free form peptides and salts thereof. The free form peptide and salt thereof can be reciprocally converted. The free form peptide can be converted to a pharmaceutically acceptable salt by reacting with an inorganic or an organic acid. The examples of the salt include the salt with the inorganic acid, such as carbonate, bicarbonate, hydrochloride, sulfate, nitrate or borate; and the salt with the organic acid, such as succinate, acetate, propionate or trifluoroacetate. Further, the salt with alkali metal such as sodium salt or potassium salt; the salt with alkali earth metal such as calcium salt or magnesium salt; the salt with organic amine such as triethylamine salt; and the salt with basic amino acid such alginic acid salt is included. The peptides of the present invention can exist as metal complex such as copper complex or zinc complex.
The form of the salt as mentioned above has an important role for the stability of the ghrelins. That is, pH values of the aqueous solution of the salts above are different from each other, and therefore, these salts play the role as pH adjuster for the aqueous solution of the ghrelins.
The origins and the manufacturing methods of the ghrelins are not limited in the present invention. The ghrelins obtained by chemical process, semichemical process, genetical process or combination process thereof, and extraction from living body can be used in the present invention.
The ghrelins to be used as raw materials for medicines are commonly supplied as lyophilized powder after purified by reverse liquid chromatography and so on.
The aqueous solution or solution of the present invention are the solution used water as the solvent; however, other solvent such as ethanol, 2-propanol and the like can be used within a pharmaceutically acceptable range.
The concentration of the ghrelins in the pharmaceutical composition of the present invention is not limited, and is preferably within a pharmaceutically acceptable range. The lower limit of concentration is the concentration wherein the ghrelins exhibit the pharmacologically activities, and the upper limit of concentration is the concentration wherein the ghrelins can be dissolve in the aqueous solutions. The concentration commonly used as medicines such as 0.03 nmol/mL to 6 µmol/mL is preferable, and more preferably, the concentration of 0.03 nmol/mL to 3 µmol/mL is used.
In the physiological composition of the present invention stably, containing the ghrelins, the pH value of the solution is in the range of 2 to 7, more preferably 3 to 6. It was found out that the stable pH value of the solution containing the ghrelins is in the range of 2 to 7. The adjustment of pH of the solution containing the ghrelins is conducted with pH adjuster or buffer agent.
Examples of pH adjuster include hydrochloric acid, sulfuric acid, nitric acid, boric acid, carbonic acid, bicarbonic acid, gluconic acid, sodium hydroxide, potassium hydroxide, aqueous ammonia, citric acid, monoethanolamine, lactic acid, acetic acid, succinic acid, fumaric acid, maleic acid, phosphoric acid, methanesulfonic acid, malic acid, propionic acid, trifluoroacetic acid, and salt thereof.
Examples of buffer agent include glycine, acetic acid, citric acid, boric acid, phthalic acid, phosphoric acid, succinic acid, lactic acid, tartaric acid, carbonic acid, hydrochloric acid, sodium hydroxide, and the salt thereof. Among them, glycine, acetic acid or succinic acid are preferably used as buffer agent.
Considering the stability of the ghrelins in the aqueous solution, it is desired that the fluctuation of pH values of the solution have to be reduced. Therefore, the pharmaceutical composition of the present invention is the solution having buffer capacity, that is, the buffer solution.
The buffer solution, having the pH range wherein the degradation of the ghrelins is inhibited is used, and the solution having the pH range of 2 to 7, more preferably 3 to 6 is used.

The suitable buffer solution is glycine hydrochloride buffer, acetate buffer, citrate buffer, lactate buffer, phosphate buffer, citric acid-phosphate buffer (including McIlvaine buffer), phosphate-acetate-borate buffer (including Britton-Robinson buffer), and phthalate buffer. The examples of the components of each buffers include the buffer agents mentioned above.

The concentration of pH adjuster is not limited and can be the concentration commonly used to adjust the solution with the desired pH range, and in general, the concentration of 0.01 to 100 mM is used.

Further, the concentration of buffer agent is also not limited and can be the concentration maintaining the buffer capacity. Generally, the concentration of 0.01 to 100 mM, preferably 0.1 to 100 mM, more preferably 1 to 100 mM is commonly used.

According to the present invention, the pharmaceutical composition stably containing the ghrelins in the aqueous solution is provided. The composition contains other additives in consideration of osmolality, solubility, low irritation of the solution, as well as antisepsis effect and prevention of absorption of the ingredient in the solution.

In general, there is fear that in the pharmaceutical aqueous solution containing peptides or proteins, the peptides or proteins adsorb to vessels used in the process for producing the solution or during the administering of the solution, and therefore, the concentration of peptides or proteins decrease. In the case of the pharmaceutical composition of the present invention, it was confirmed that the ghrelins adsorb to glass vessels or polypropylene vessels in the range of the concentration of the ghrelins for medical use. Therefore, it is preferable to contain the anti-adsorbent to prevent the adsorption of the ghrelins to vessels. Examples of anti-adsorbent include surfactants, saccharides, amino acids and proteins.

The surfactant of the present invention include the surfactants listed in the "Handbook of PHARMACEUTICAL EXCIPIENTS" as well as the compounds having surface-active effects, and the suitable surfactant is select from these surfactants. Examples include quaternary ammonium salts, polyoxyethylene sorbitan fatty acid esters, sorbitan fatty acid esters, parabens, polyethylene glycols, phospholipids, bile acids, polyoxyethylene castor oils, polyoxyethylenes, polyoxyethylene polyoxypropylenes, polyalcohols, anionic surfactant, synthetic or semi-synthetic polymers. Among them, polyoxyethylene sorbitan fatty acid esters and sorbitan fatty acid esters are preferably used.

The suitable quaternary ammonium salts include benzalkonium chloride, benzethonium chloride and cetylpyridinium chloride.

The suitable polyoxyethylene sorbitan fatty acid esters include polyoxyethylene sorbitan monolaurate (Polysorbate® 20 or Tween® 20), polyoxyethylene sorbitan monopalmitate (Polysorbate® 40 or Tween® 40), polyoxyethylene sorbitan monostearate (Polysorbate® 60 or Tween® 60), polyoxyethylene sorbitan tristearate (Polysorbate® 65 or Tween® 65), polyoxyethylene sorbitan monooleate (Polysorbate® 80 or Tween® 80), and polyoxyethylene sorbitan trioleate (Polysorbate® 85 or Tween® 85).

The suitable sorbitan fatty acid esters include sorbitan monolaurate (Span®20), sorbitan monopalmitate (Span®40), sorbitan monostearate (Span® 60), sorbitan monooleate (Span® 80), sorbitan trioleate (Span® 85), and sorbitan sesquioleate.

The suitable parabens include methyl paraoxybenzoate, ethyl paraoxybenzoate, propyl paraoxybenzoate, butyl paraoxybenzoate, and isobutyl paraoxybenzoate.

The suitable polyethylene glycols include glycofurol (glycofurol 75), Mcrogol® 400 (polyethylene glycol 400), Mcrogol® 600 (polyethylene glycol 600), and Mcrogol® 9000 (polyethylene glycol 9000); the suitable phospholipids include refined soybean lecithin and refined yolk lecithin; and suitable bile acids include sodium desoxycholic acid.

The suitable polyoxyethylene castor oils include polyoxyethylene castor oil, polyoxyethylene hydrogenated castor oil, polyoxyethylene hydrogenated castor oil 50, and polyoxyethylene hydrogenated castor oil 60. Examples of other polyoxyethylenes include polyoxyethylene oleyl ether, polyoxyethylene stearyl ether, polyoxyethylene cetyl ether, and polyoxyethylene lauryl sulfate salt.

The suitable polyoxyethylene polyoxypropylenes include polyoxyethylene polyoxypropylene glycol (Pluronic®) and polyoxyethylene polyoxypropylene cetyl ether.

The suitable polyalcohols include glycerin (glycerol), propylene glycol, and monoglyceryl stearate; and the suitable anionic surfactants include alkyl ether sulfate such as sodium cetyl sulfate, sodium lauryl sulfate and sodium oleyl sulfate; alkyl sulfosuccinate such as sodium lauryl sulfosuccinate. The suitable synthetic or semi-synthetic polymers include polyvinyl alcohol, carboxyvinyl polymer, polyvinyl pyrrolidone and sodium polyacrylate.

Examples of saccharides include monosaccharide such as mannitol, glucose, fructose, inositol; sorbitol, and xylitol; disaccharide such as lactose, sucrose, maltose, and trehalose; polysaccharide such as starch, dextran, pullulan, alginic acid, hyaluronic acid, pectinic acid, phytic acid, phytin, chitin, and chitosan. Examples of dextrin include α-cyclodextrin, β-cyclodextrin, γ-cyclodextrin, dextrin, hydroxypropyl starch, and hydroxyl starch. Examples of celluloses include methylcellulose, ethylcellulose, hydroxyethyl cellulose, hydroxypropyl cellulose, and hydroxypropyl methylcellulose, sodium carboxymethyl cellulose.

The suitable amino acids include glycine and taurine; and polyamino acid such as polyglutamic acid, polyaspartic acid, polyglycine and polyleucine. The Examples of proteins include albumin and gelatin.

Non-human serum albumin can be used as anti-adsorbent for the pharmaceutical composition of the present invention when the composition is used as a reagent for examination or as veterinary medicines; however, it is preferable to use human serum albumin when the composition is used for a medicine for treating human being.

These anti-adsorbents can be used in combination. The concentration of the anti-adsorbent is in the range wherein the amount of the anti-adsorbent is pharmaceutically acceptable one and the adsorption of the ghrelins to the vessel is inhibited and the aggregation of the components does not occur during the manufacturing process or the long-term storage. For example, the concentration of the anti-adsorbent is in the range of 0.001 to 5%, preferably from 0.01 to 1%.

The pharmaceutical composition of the present invention can contain further additives for any purpose, and examples of the additives is selected from the "Handbook of PHARMACEUTICAL EXCIPIENTS 2000" (Japan Pharmaceutical Excipients Council: Yakuji Nippoh Sha). These include isotonizing agent such as sodium chloride and mannitol; antiseptic agent such as sodium benzoate; antioxidant such as sodium bisulfite, sodium pyrosulfite and ascorbic acid; soothing agent such as lidocaine hydrochloride and mepivacaine hydrochloride.

The manufacture of the pharmaceutical composition of the present invention is conducted by mean of the common procedure applied in the pharmaceutical field. For example, first, freeze dried ghrelin is dissolved in the purified water, and then, buffer agent, anti-adsorbent and other additives are also dissolved in another purified water. Then the resulting water solutions are combined and sterilize by filtration if necessary, and the obtained solution is filled in ampoules or vials to obtain the pharmaceutical composition containing the ghrelins of the present invention.

As the dosage form for the injectable preparation, there is in situ preparation for the pharmaceutical composition. This dosage form is suitable for the compound, which is unstable in the solution for long-term storage. Therefore, the composition to prepare the solution containing the ghrelins in situ is one of the injectable preparations of the present invention. The composition to prepare the solution containing the ghrelins in situ can contain raw material of the ghrelins for medicines and other additives with necessary amounts in a solid state. Further, the composition is obtained by drying the solution containing the ghrelins and other additives with necessary amounts. The dry technique of the solution can be the freeze-drying method or the spray drying method, and the freeze-drying method is preferred. These solid compositions can be used as the solution with water in situ.

The pharmaceutical composition of the present invention can be administered to the mammal (human, monkey, dog, mouse and so on) as medicine. The applicable diseases or obtainable efficacies of the composition are the diseases concerning the deficient or decreasing growth hormone (GH) such as dwarfism, activating osteoblast or osteoanagenesis in normal adult, build-up of muscle quantity and muscle strength, improvement of physical capabilities in GH deficiency of adult, severe schizophrenia in childhood, use in combination with gonadotropin for induction of ovulation, prevention of protein metabolic disorder by administration of prednisone, acceleration of T-cell training in severe immune deficiency disease, senile loss weight, and prevention of adipes enlargement and atrophy cutis.

Further, examples of the applicable diseases or obtainable efficacies indirectly concerning the deficient or decreasing growth hormone (GH) include cardiovascular disease such as cardiac failure based on the increasing effect of heart rate of the pharmaceutical composition of the present invention. The effects of the pharmaceutical composition of the present invention are not limited to the human being, and are growth promotion of animals, reducing of fat, and so on, and these effects are more strong than those obtained by administering GH. The pharmaceutical composition of the present invention my use as appetite enhancer for treating anorexia or anorexia nervosa by intravenously or intracerebroventricular administering due to the improvement in one's appetite. Further, the pharmaceutical composition of the present invention my use for treating the dynamic disorder of stomach such as non-ulcerous apepsia, idiopathic mild gastric atony, dynamic apepsia and reflux esophagitis.

Furthermore, the pharmaceutical composition of the present invention exerts the acceleration effect of cell growth in bone marrow, intestine duodenum and intestinum jejunum, and therefore, use as protectant for intestinal mucosa, mucosa injury preventive agent in small intestine during intravenously furnishing of nutrition, and osteoporosis.

Further, the pharmaceutical composition of the present invention may for treating the following diseases, or improving the following bodily functions. The examples of these diseases include stimulation of releasing growth hormone in aged person, prevention of catabolic side effect of glucocorticoid, treating and preventing of osteoporosis, stimulation of immune system, promotion of curing the injury, promotion of repair the bone fracture, treating for growth delay, treating for renal failure or malfunction due to growth delay, treating for the physiologically missing condition including deficiency of growth hormone in children and related to chronic ailment, treating for growth delay with adiposis or growth delay related to adiposis, treating for growth delay related to Prader-Willi syndrome and Turner's syndrome, promotion of recovery from burn injury and cut-back admission to hospital, growth delay uterine, skeletal dysplasia, treating for hypercorticoidism and Cushing's syndrome, induction of systaltic growth hormone, substitution of growth hormone in stress patient, cartilaginous dysplasia, Noonan's syndrome, schizophrenia, ademonia, Alzheimer's disease, curing of delayed damages and therapy of psychosocial deprivation, therapy of insufficiency of lung function and respiratory dependence syndrome, decay of catabolism reaction of proteins after major surgery, protein loss and decrease of cachexia due to the chronic diseases such as cancer or AIDS, therapy of hyperinsulinaemia including nesidioblastosis, adjuvant therapy for induction of ovulation, stimulation for development of thymus, preventing the age-related atrophy of thymus function, therapy for patients with impaired immune systems, strength of muscle, improvement of motility, skin thickening of elderly people, metabolic homeostasis, maintenance of renal homeostasis, stimulating osteoblast, osteoanagenesis and chondrogenesis.

Further, in animals the pharmaceutical composition of the present invention is effective for growth promotion of animals, increasing milk and animal hair production, activation of immunologic systems of pet animal, therapy for age-related diseases of pet animal, growth promotion of farm animals, and increasing mutton hair production.

The pharmaceutical composition of the present invention is administered by various kinds of administering route with an aqueous solution. For example, the pharmaceutical composition of the present invention is administered in the form of injectable solution such as intravenous injection, subcutaneous injection, intramuscular injection or intravenous drip. Further, the pharmaceutical composition of the present invention is administered by parenteral route such as nasal route, transpulmonary route, transdermic route or transmucosal route. Furthermore, the pharmaceutical composition of the present invention is parenterally administered in the form of ophthalmic solution or capsule filled with the solution.

EXAMPLE

The stability of the ghrelins of the present invention is illustrated in more detail by way of the following Tests and Examples, but it is to be noted that the present invention is not limited by those tests and examples in any way.

In the following description, the following symbols are used to have the particular meanings and the following test methods and the instruments are used while it is not stated otherwise.

[Symbols]
Dha: dehydroalanine
TEA: trifluoroacetic acid
HBTU: 2-(1H-benzotriazole-1-yl)-1,1,3,3-tetramethyl-uronium hexafluorophosphate
HOBt: 1-hydroxybenzotriazole
TIPS: tri-isopropylsilane
DIPEA: diisopropylethylamine
Fmoc: fluorenylmethoxycarbonyl
Boc: t-butyloxycarbonyl
tBu: t-butyl
Trt: trityl
DMAP: 4-dimethylaminopyridine
EDC: 1-ethyl-3-(3-dimethylaminopropyl)carbodiimide
Pmc: 2,2,5,7,8-pentamethylchroman-6-sulfonyl

[Instruments]
(A) Automatic Peptide Synthesizer
   Applied'Biosystems: Automatic 433A peptide synthesizer
(B) HPLC Systems for Analysis
   Instrument: Shimadzu LC-10A system
   Column: YMC-Pack PROTEIN-RP (4.6 mmΦ×150 mm)
      or
      YMC-Pack ODS-AM (4.6 mmΦ×250 mm)
   Column temperature: 40° C.
   Eluent: acetonitrile in 0.1% TFA, with linear gradient of max 50% concentration.
   Flow rate: 1 mL/min
   Detection: UV (210 nm)
   Loaded volume: 10 to 500 μL
(C) HPLC Systems for Aliquot
   Instrument: Waters 600 Multisolvent Delivery System
   Column: YMC-Pack ODS-A (20 mmΦ×250 mm) or
      YMC-Pack PROTEIN-RP (20 mmΦ×250 mm)
   Eluent: acetonitrile in 0.1% TFA or 5% acetic acid, with linear gradient.
   Flow rate: 10 mL/min
   Detection: UV (210 and 260 nm)
   Loaded volume: 1 to 2 mL (more than 2 mL, loaded by pump)
(D) Storage Chamber
   Constant temperature and humidity chamber LH-30 (Nagano Kagaku) 5° C./40° C.
   Prefab type constant temperature and humidity chamber LH-20 (Nagano Kagaku) 25° C.
(E) Mass Spectrum
   Instrument: Finnigan MAT TSQ700
   Ion source: ESI
   Detective ion mode: positive
   Spray voltage: 4.5 kV
   Capillary temperature: 250° C.
   Mobile phase: 0.2% acetic acid in $H_2O$/methanol (1/1)
   Flow rate: 0.2 mL/min
   Scan area: m/z 300 to 1500
(F) Analysis of Amino Acid Sequence
   Instrument: Applied Biosystem 477A Sequencer (Perkin-Elmyer)
(G) Analysis of Amino Acid Composition
   Instrument: Amino acid analyzer L-8500 (Hitachi)
   Sample: Hydrolyzed with 6M-HCl containing 0.1% phenol in sealed tube at 110° C. for 24 hours.

Reference Example

Synthesis of Human Ghrelin

Using the Automatic peptide synthesizer, Boc-Gly-Ser(tBu)-Ser(Trt)-Phe-Leu-Ser(tBu)-Pro-Glu(OtBu)-His(Boc)-Gln(Trt)-Arg(Pmc)-Val-Gln(Trt)-Gln(Trt)-Arg(Pmc)-Lys(Boc)-Glu(OtBu)-Ser(tBu)-Lys(Boc)-Lys(Boc)-Pro-Pro-Ala-Lys(Boc)-Leu-Gln(Trt)-Pro-Arg(Pmc)-HMP resin was synthesized from Fmoc-Arg(Pmc)-HMP-resin (Applied Biosystems Japan; 472 mg, 0.25 mmol) by repeated deletion of Fmoc and insertion of Fmoc-amino acid (provide that, Boc-glycine was used in the case of glycine N-terminal) by HBTU/HOBt. The obtained protected peptide-resin (1.7 g) was treated with 1% TFA/5% TIPS/methylene chloride solution (15 mL) for 30 minutes. The peptide-resin was collected and washed with methylene chloride (30 mL) for several times, and with 1% DIPEA (30 mL) then with methylene chloride (30 mL). The obtained Trt deleted peptide-resin was swelled in N-methylpyrrolidone (10 mL) and the mixture was reacted with octanoic acid (144.2 mg, 1.01 mmol) and EDC-HCl (192 mg, 1.0 mmol) in the presence of DNAP (31 mg, 0.25 mmol) for 16 hours. The resulting resin was collected by filtration and washed with N-methylpyrrolidone and methylene chloride respectively, and dried in vacuo to obtain protected peptide-resin wherein side chain of serine at 3-position was substituted by octanoyl group. Then, deprotection reagent consisting of 88% TFA/5% phenol/2% TIPS/5% $H_2O$ (15 mL) was added to the obtained resin and the mixture was stirred for 2 hours at room temperature. The resin was removed off by filtration and the filtrate was concentrated. The obtained residue was treated with ether to give the precipitate, and collected by filtration. The precipitate was dried to give 900 mg of crude peptide. 200 mg of the obtained crude peptide was dissolved in 10 mL of water and the solution was added to MC-Pack ODS-A column (20 mmΦ×250 mm) and eluted by 5% TFA with linear gradient of 0 to 60% of acetonitrile for 60 minutes (flow rate: 10 mL/min). The objective eluted parts were collected and lyophilized to give 60 mg of target peptide (human ghrelin acetic acid salt:acetic acid content: 10.9%). ESI-MS: 3371 (calculated: 3370.9)
Leu standard amino acid composition: Ser; 3.43 (4), Glx; 5.93 (6), Gly; 1.01 (1), Ala; 1.00 (1), Val; 0.98 (1), Leu; 2 (2), Phe; 1.00 (1), Lys; 4.02 (4), His; 1.00 (1), Arg; 2.98 (3), Pro; 3.93 (4) (theoretical volume are in parentheses).
Analysis of amino acid sequence: The obtained peptide is identified with human ghrelin (octanoyl-Ser at 3 position not detected).
Rat ghrelin or other the ghrelins were obtained by using the same procedure mentioned above.
In the following Example, the ghrelins obtained by the Reference Example was used.

Example 1

Structural Analysis of the Degradation Products of the Ghrelins

It is necessary to know the degradation reaction of the ghrelins in the aqueous solution to secure the stability of ghrelin in the aqueous solution. Therefore, the degradation process of ghrelin was estimated by the structural analysis of the degradation products of the ghrelins by using human ghrelin, which is one of the ghrelins.
The aqueous solution containing about 0.15 μmol/mL (0.5 mg/mL) of human ghrelin was obtained by dissolving about 5.0 μmol (17 mg) of human ghrelin in Britton-Robinson buffer solution (pH 7.0: adjusted by 0.04M of phosphate/acetic acid/boric acid solution) and 0.2M sodium hydroxide aqueous solution. The obtained solution was filled in brownish glass ampoules and the ampoules were sealed with fire. The each ampoules were stored at 40±1° C. for 4 and 14 days. The degradation products in the aqueous solutions after storage were detected by HPLC method and the results were shown in FIGS. 1 (a) and (b).
As shown in FIG. 1 (a), 2 major peaks (degradation product B and degradation product C) at 24 to 28 minutes were observed in the solutions after stored at 40° C. for 4 days. The two degradation product B and degradation product C were collected and the structural analysis of these degradation products from human ghrelin was conducted as follow.
The Degradation Product B:
The mass of this product showed 3245 by ESI-MS analysis, and was identified with the mass of desacylated human ghrelin (hereinafter, referred to as "desacyl compound") obtained from the hydrolytic cleavage of octanoyl group of human ghrelin. Further, from the results of amino acid sequence and amino acid composition analysis of the degradation product B, the amino acid composition and the amino acid sequence were identified with the theoretical volume of those of desacyl compound. In conclusion, it was confirmed that the degradation product B was desacyl compound.

The Degradation Product C:

The mass of this product showed 3227 by ESI-MS analysis, and was identified with the mass of [3-Dehydroalanine] human ghrelin (hereinafter, referred to as "Dha compound") obtained from the β-elimination of octanoyl group of human ghrelin. Further, from the results of ESI-MS, amino acid sequence and amino acid composition analysis of the product obtained by the degradation product C by reacting with excess ethanethiol in an aqueous solution neutralized with 0.05M sodium hydroxide aqueous solution, the product was identified with [3-Ethylcysteine]human ghrelin. That is, the mass of 3289 by ESI-MS was identified with the calculated addition value of Dha compound (3227) and ethanethiol (62), and ethylcysteine was detected from amino acid sequence and amino acid composition analysis. The product, [3-Ethylcysteine]human ghrelin, was obtained from Dha compound by nucleophilic reaction of ethanethiol. In conclusion, it was confirmed that the degradation product C was Dha compound.

From the above-mentioned results, it was confirmed that the degradation products in the neutralized aqueous solution of human ghrelin, which is one of the ghrelins, were desacyl compound obtained from the hydrolytic cleavage of octanoyl group of human ghrelins and Dha compound obtained from the β-elimination of octanoyl group of human ghrelin.

As shown in FIG. 1 (b), the HPLC results of the solution stored for 14 days, several peaks (degradation product D, E and so on) were observed in addition to peaks of degradation product B and C. Then, the desacyl compound (degradation product B) and the Dha compound (degradation product C) were stored in aqueous solution to examine the mechanism of production of these degradation products.

The desacyl compound or the Dha compound was dissolved in Britton-Robinson buffer solution (pH 7.0) to prepared an aqueous solution containing about 0.15 μmol/mL (0.5 mg/mL) of the desacyl compound or the Dha compound in same manner described above. The obtained solution was filled in brownish glass ampoules and the ampoules were sealed with fire. The ampoules filled with desacyl compound were stored at 40±1° C. for 14 days, and the ampoules filled with Dha compound were storage at 40±1° C. for 3 days. The degradation products in the aqueous solutions after stored were detected by HPLC method and the results were shown in FIGS. 1 (c) and (d).

As shown in FIG. 1 (c), one major peak at the same retention time (26 minutes) as that of degradation product D in FIG. 1 (b) was observed in the solutions containing desacyl compound, after stored at 40° C. for 14 days. The degradation product at this peak was collected and ESI-MS, amino acid sequence and amino acid composition analysis were conducted. From the results of these analyses, this product was identified with desacyl human ghrelin (3-28).

ESI-MS: 3101 (calculated value: 3100.5).

Further, as shown in FIG. 1 (d), one broad peak at the same retention time (36 minutes) as that of degradation product E in FIG. 1 (b) was observed in the solutions containing Dha compound, after stored at 40° C. for 3 days. The degradation product at this peak was collected and ESI-MS, amino acid sequence and amino acid composition analysis were conducted. From the results of these analyses, this product was estimated to be [$N^\alpha$—CO—C(=$CH_2$)—OH]human ghrelin (4-28) (hereinafter, referred to as "2nd degradation product of Dha compound").

ESI-MS: 3083 (calculated value: 3083.5),

Amino acid composition: Identified with the estimated amino acid composition.

Amino acid sequence: No reaction from first amino acid residue.

Furthermore, in FIG. 1 (d), several small peaks were observed at about 30 to 35 minutes. These peaks were also observed in FIG. 1 (b), and it was estimated that these degradation products were produced from human ghrelin via Dha compound.

From the above-mentioned results, the degradation process of the aqueous solution containing human ghrelin was confirmed that the desacyl compound or the Dha compound was produced from human ghrelin at the beginning, and then, the desacyl human ghrelin (3-28) was produced by fragmentation of the desacyl compound and 2nd degradation product of Dha compound and further products were produced by fragmentation of the desacyl compound, respectively.

Therefore, it was confirmed that to obtain the stability of the ghrelins in an aqueous solution, it was necessary to prevent the various type of cleavage reactions at the hydrophobic group, which was the characteristic structure of the ghrelins.

Example 2

Stability of the Ghrelins in Buffer Solutions Having Various Kinds of pH Value (Stability Test 1)

The influence of pH value of the solution containing the ghrelins was conducted using human ghrelin, which is one of the ghrelins.

Human ghrelin was dissolved in the following aqueous solutions in the concentration of about 0.15 mmol/mL (0.5 mg/mL).

0.1M HCl aqueous solution (pH: 1.1)

McIlvain buffer solutions (pH: 2.0, 3.0, 4.0, 5.0, 6.0, 7.0, 8.0)

The pH was adjusted with 0.1M citric aqueous acid and 0.2M dibasic sodium phosphate aqueous solution.

Each solution were stored at 25±2° C. for 8, 24, 48 and 72 hours respectively, and the obtained solutions were detected by HPLC analysis in comparison to the solutions before storage. The peak area ratio of human ghrelin, desacyl compound and Dha compound to the total area were calculated. No significant changes of pH in solution before storage and after storage were observed. The results were shown in Table 2.

TABLE 2

| | | | Peak area ratio to total peak area (%) | | |
|---|---|---|---|---|---|
| | | pH observed | Human ghrelin[a] | Desacyl compound[b] | Dha compound[b] |
| pH 1 | Before | 1.1 | 98.89 | 0.27 | 0.21 |
| | 8 hr. after | 1.2 | 94.40 | 4.88 | 0.15 |
| | 24 hr. after | 1.2 | 86.00 | 13.31 | 0.09 |
| | 48 hr. after | 1.2 | 74.62 | 24.63 | 0.04 |
| | 72 hr. after | 1.2 | 65.04 | 34.17 | 0.00 |
| pH 2 | Before | 2.0 | 99.07 | 0.10 | 0.20 |
| | 8 hr. after | 2.0 | 98.82 | 0.34 | 0.20 |
| | 24 hr. after | 2.0 | 98.24 | 0.89 | 0.23 |
| | 48 hr. after | 2.0 | 97.35 | 1.76 | 0.24 |
| | 72 hr. after | 2.0 | 96.46 | 2.59 | 0.25 |
| pH 3 | Before | 3.0 | 99.07 | 0.10 | 0.20 |
| | 8 hr. after | 3.1 | 98.98 | 0.20 | 0.20 |
| | 24 hr. after | 3.1 | 98.77 | 0.38 | 0.23 |
| | 48 hr. after | 3.1 | 98.40 | 0.67 | 0.24 |
| | 72 hr. after | 3.1 | 98.03 | 0.98 | 0.25 |

TABLE 2-continued

| | | pH observed | Peak area ratio to total peak area (%) | | |
|---|---|---|---|---|---|
| | | | Human ghrelin[a] | Desacyl compound[b] | Dha compound[b] |
| pH 4 | Before | 4.0 | 99.07 | 0.09 | 0.20 |
| | 8 hr. after | 4.0 | 99.07 | 0.12 | 0.20 |
| | 24 hr. after | 4.0 | 98.92 | 0.21 | 0.21 |
| | 48 hr. after | 4.0 | 98.69 | 0.37 | 0.22 |
| | 72 hr. after | 4.0 | 98.44 | 0.51 | 0.23 |
| pH 5 | Before | 5.0 | 99.06 | 0.10 | 0.21 |
| | 8 hr. after | 5.0 | 99.04 | 0.14 | 0.21 |
| | 24 hr. after | 5.0 | 98.91 | 0.24 | 0.21 |
| | 48 hr. after | 5.0 | 98.59 | 0.45 | 0.23 |
| | 72 hr. after | 5.0 | 98.37 | 0.61 | 0.24 |
| pH 6 | Before | 6.0 | 99.07 | 0.10 | 0.20 |
| | 8 hr. after | 6.0 | 98.87 | 0.28 | 0.21 |
| | 24 hr. after | 6.0 | 98.28 | 0.70 | 0.26 |
| | 48 hr. after | 6.0 | <u>97.64</u> | <u>1.33</u> | 0.31 |
| | 72 hr. after | 6.0 | 96.92 | 1.97 | 0.35 |
| pH 7 | Before | 7.0 | 98.97 | 0.16 | 0.22 |
| | 8 hr. after | 7.0 | 98.15 | 0.92 | 0.25 |
| | 24 hr. after | 7.0 | <u>96.18</u> | <u>2.70</u> | 0.43 |
| | 48 hr. after | 7.0 | <u>93.44</u> | <u>5.22</u> | 0.61 |
| | 72 hr. after | 7.0 | 90.75 | 7.67 | 0.79 |
| pH 8 | Before | 8.0 | 98.61 | 0.47 | 0.24 |
| | 8 hr. after | 7.9 | <u>94.73</u> | <u>3.92</u> | 0.68 |
| | 24 hr. after | 7.9 | <u>87.32</u> | <u>10.57</u> | <u>1.39</u> |
| | 48 hr. after | 7.9 | <u>76.95</u> | <u>19.54</u> | <u>2.39</u> |
| | 72 hr. after | 7.9 | 68.30 | 27.26 | 3.12 |

[a]The place where ratio of peak area of human ghrelin is below 98% is under lined.
[b]The place where ratio of peak area of desacyl compound or Dha compound below 1% is under lined.

As shown in Table 2 above, more than 3% of the desacyl compound was produced in the aqueous solution of human ghrelin at pH 1.0 and 8.0 in the shortest time, such as storage for 8 hours. Further, more than 1% of the desacyl compound was produced in the aqueous solution of human ghrelin at pH 7.0 stored for 24 hours and at pH 2.0 and 6.0 stored for 48 hours, and ratio of human ghrelin was less than 98%. On the contrary, the production of the desacyl compound and the Dha compound was inhibited in the solution having the pH range of 3.0 to 5.0.

It was understood that the aqueous solution having the pH range of 2 to 7, preferably 3 to 6 was suitable for inhibiting the production of the desacyl compound and the Dha compound. Therefore, it was confirmed that to obtain the stability of the ghrelins in an aqueous solution, it was necessary to adjust the pH of the solution to the range of 2 to 7, preferably 3 to 6 to prevent the various type of cleavage reactions at the hydrophobic group, which is the characteristic structure of the ghrelins.

Example 3

Stability of the Ghrelins in Buffer Solutions Having Various Kinds of pH Value (Stability Test 2)

Using different buffer solution from the buffer solution of the Example 2, the stability of the ghrelins was conducted in the buffer solution having various kinds of pH value.

Human ghrelin, which is one of the ghrelins, was dissolved in the Britton-Robinson buffer solutions which is adjusted by combining 0.04M phosphoric acid-acetic acid-boric acid aqueous solution and 0.2M sodium hydrate aqueous solution in appropriate ratio, having pH of 2.1, 3.1, 4.0, 5.0, 6.0, 7.0 and 7.9 to obtain an aqueous solution containing human ghrelin in the concentration of about 0.15 μmol/mL (0.5 mg/mL). The obtained solution was filled in brownish glass ampoules and the ampoules were sealed with fire. For the calculation of kinetic constant, the certain degrees of degradation products have to be occurred in the aqueous solution of the ghrelins, and therefore, the ampoules were stored at 40±1° C., which was severe conditions for storage. The concentration (residual ratio) of human ghrelin was conducted by HPLC with time. At the same time, the pH of the solution was measured and it was confirmed that there was no significant changes of pH in solution.

Figure 2:
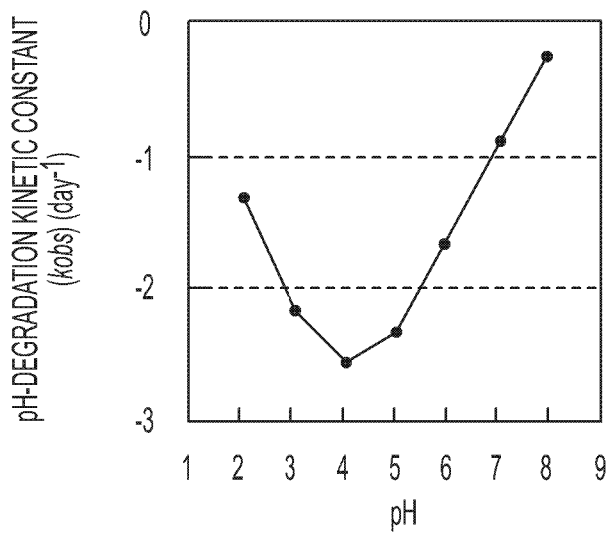
FIG. 2 is the graphic chart showing the profile of pH-degradation kinetic constant of the ghrelins.

The kinetic constants in each pH solution were calculated from the sequential change of the residual ratio, and the results were shown in FIG. 2.

Figure 3:
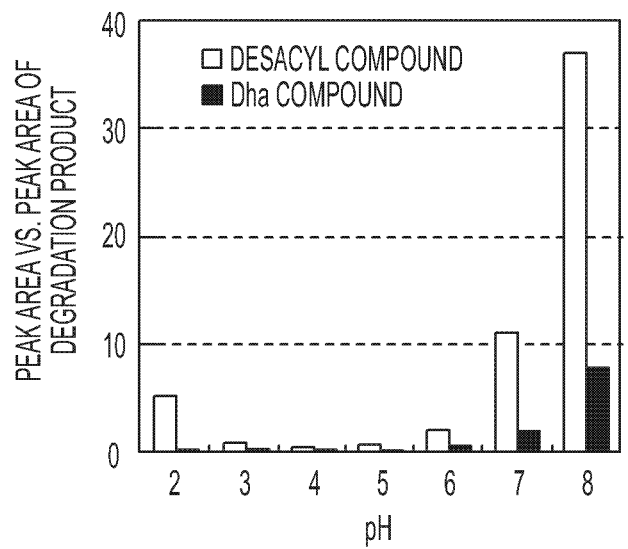
FIG. 3 is the graphic chart showing the production amount of the degradation product of the ghrelins in aqueous solution having various kinds of pH.

Further, the peak area ratios of desacyl compound and Dha compound to the total area in each solution having various kinds of pH, after stored at 40° C. for 1 day, were shown in FIG. 3.

As shown in FIG. 2, it was confirmed that the pH range of the solution stably containing human ghrelin was from 3 to 6. The residual ratios of ghrelin in the solutions having the pH of 3.1, 4.0, 5.0 and 6.0 were more than 87%, and these value were exceeded the target value (85%).

Further, as shown in FIG. 3, the production of desacyl compound was inhibited in the solution having the pH range of 3 to 6, and the production of Dha compound was inhibited in the solution having the pH range of 2 to 7.

From the results mentioned above, it was understood that in the case of using Britton-Robinson buffer solution, the aqueous solution having the pH range of 2 to 7, preferably 3 to 6 was suitable for inhibiting the production of the desacyl compound and the Dha compound. Therefore, it was confirmed that to obtain the stability of the ghrelins in an aqueous solution, it was necessary to adjust the pH of the solution to 2 to 7, preferably 3 to 6 to prevent the various type of cleavage reactions at the hydrophobic group, which was the characteristic structure of the ghrelins.

Example 4

The Influence of the Varieties of Buffer Solution for Stability of the Ghrelins (Test 1)

The stability of the ghrelins by using citrate buffer solution was examined.

Human ghrelin, which is one of the ghrelins, was dissolved in the citrate buffer solutions having pH of 3.6, 4.0, 4.5 and 5.0 to obtain an aqueous solution containing human ghrelin in the concentration of about 0.15 μmol/mL (0.5 mg/mL). The obtained solutions were filled in brownish glass ampoules and the ampoules were sealed with fire, then, each ampoules were stored at 40±1° C. for 2 weeks. After storage for 2 weeks, the HPLC analysis of the solutions was conducted to calculate the residual ratio from the concentration of human ghrelin. The change of pH value was also measured.

These results were summarized in the following Table 3.

TABLE 3

| pH of buffer solution | | Just after preparation | After storage for 40° C./2 weeks |
|---|---|---|---|
| 3.5 | Residual ratio (%) | 100 | 89 |
| | pH (observed) | 3.6 | 3.5 |
| 4.0 | Residual ratio (%) | 100 | 88 |
| | pH (observed) | 4.0 | 4.0 |
| 4.5 | Residual ratio (%) | 100 | 86 |
| | pH (observed) | 4.5 | 4.4 |
| 5.0 | Residual ratio (%) | 100 | 85 |
| | pH (observed) | 5.0 | 4.9 |

As shown in Table 3, the residual ratios of human ghrelin were from 85 to 89% when human ghrelin was dissolved in citrate buffer solutions having the pH range of 3.5 to 5.0, and these values exceeded the target value (85%). Further, no significant changes of pH in solution before storage and after storage were observed. Therefore, it was confirmed that the stability of the ghrelins in citrate buffer solution was obtained in the pH range of 3.5 to 5.0.

Example 5

The Influence of the Varieties of Buffer Solution for Stability of the Ghrelins (Test 2)

The stability of the ghrelins was examined by using glycine hydrochloride buffer solution or acetate buffer solution.

Human ghrelin, which is one of the ghrelins, was dissolved in the 0.05M glycine hydrochloride buffer solutions having pH of 2.5, 3.1, 3.6, 4.2, 4.6 and 4.8, or in the 0.05M acetate buffer solution having pH of 3.1, 3.5, 4.0, 4.5 and 5.0, to obtain an aqueous solution containing human ghrelin in the concentration of about 0.15 μmol/mL (0.5 mg/mL). The obtained solutions were tilled in brownish glass ampoules and the ampoules were sealed with fire, then, each ampoules were stored at 40±1° C. for 2 weeks. After storage for 2 weeks, the HPLC analysis of the solutions was conducted to calculate the purity. The change of pH value was also examined to confirm no significant changes of pH of solution occurred.

Figure 4:
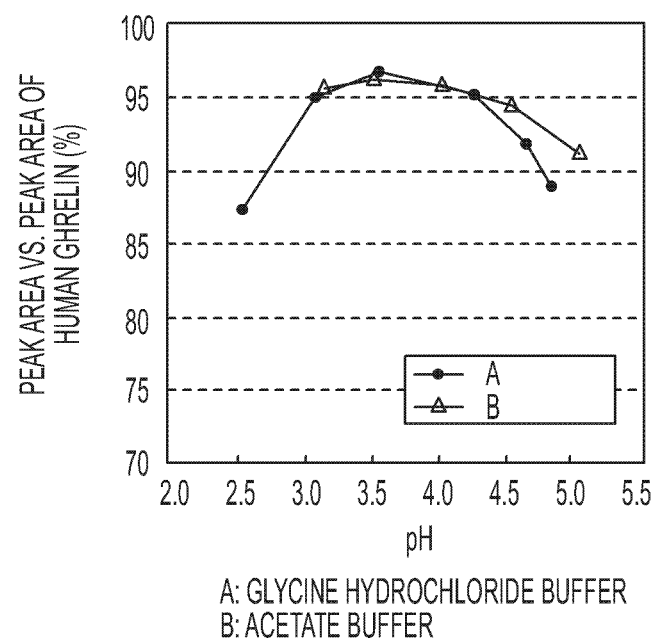
FIG. 4 is the graphic chart showing pH stability of the ghrelins in various kinds of buffer solution.

The residual ratios of human ghrelin in the each buffer solution of various kinds of pH after storage for 2 weeks were summarized in FIG. 4.

As shown in FIG. 4, the residual ratios of human ghrelin were from 87 to 97% when human ghrelin was dissolved in glycine hydrochloride buffer solution or acetate buffer solution having the pH range of 2.5 to 5.0, and these values exceeded the target value (85%).

From the results of the Example 2 (stability in McIlvaine buffer solution), the Example 3 (stability in Britton-Robinson buffer solution), the Example 4 (stability in citrate buffer solution), and the Example 5 (stability in glycine hydrochloride or acetate buffer solution), it was confirmed that the pH adjustment of the solution was important to obtain the stability of the ghrelins in aqueous solution, and the variety of buffer solution had no effect on the stability of the ghrelins in aqueous solution.

Example 6

Stability of the Ghrelins in Aqueous Solution with Various Kinds of Concentrations The stability of the ghrelins in aqueous solution with various kinds of concentration was examined.

Human ghrelin, which is one of the ghrelins, was dissolved in the 0.05M glycine hydrochloride buffer solutions (pH 3.5) to obtain an aqueous solution containing human ghrelin with following five concentrations, which are applicable for medical usage.

0.03 nmol/mL (0.1 μg/mL); 0.3 nmol/mL (1.0 μg/mL); 3.0 nmol/mL (10.0 μg/mL); 0.3 μmol/mL (1.0 mg/mL); 3 μmol/mL (10 mg/mL).

Each solutions were stored at 25±2° C. for 24 hours, and after storage, the HPLC analyses of each solutions were conducted to calculate the residual ratios from the concentration of human ghrelin. The changes of pH value were also examined to confirm no significant changes of pH in solutions occurred.

The residual ratio of the solution before storage was referred to as 100%, and the residual ratio of each solution after storage and the changes of pH value of each solution were summarized in the following Table 4.

TABLE 4

| Concentration of h. ghrelin | | Just after preparation | After storage for 25° C./24 hours |
|---|---|---|---|
| 0.03 nmol/mL | Residual ratio (%) | 100 | 62 |
| | pH | 3.4 | 3.5 |
| 0.3 nmol/mL | Residual ratio (%) | 100 | 98 |
| | pH | 3.5 | 3.5 |
| 3.0 nmol/mL | Residual ratio (%) | 100 | 98 |
| | pH | 3.5 | 3.6 |
| 0.3 μmol/mL | Residual ratio (%) | 100 | 101 |
| | pH | 3.4 | 3.3 |
| 3 μmol/mL | Residual ratio (%) | 100 | 101 |
| | pH | 3.4 | 3.3 |

As shown in Table 4, the solutions with high concentration of human ghrelin (0.3 nmol/mL, 3.0 nmol/mL, 0.3 μmol/mL and 3 μmol/mL) kept the stability of human ghrelin in the aqueous solutions during the storage at 25° C. for 24 hours, and no decrease of the residual ratios and the changes of pH value were observed.

On the contrary, in the case of the solution with low concentration of human ghrelin (0.03 nmol/mL), the residual ratio of the solution after storage was 62%; however, no significant change of pH value was observed and there was no degradation product such as desacyl compound or Dha on the HPLC chart analysis. Therefore, it was confirmed that the decrease of the residual ratio of human ghrelin in the solution might be the decrease of the content of human ghrelin due to its adsorption to the wall of the vessel. Accordingly, it was decided that the solutions with low concentration of human ghrelin (0.03 nmol/mL) also kept the stability of human ghrelin in the aqueous solution during the storage at 25° C. for 24 hours.

In conclusion, it was confirmed that the ghrelins were stably contained in the pH adjusted buffer solution in the concentration range of about 0.03 nmol/mL to about 3 μmol/mL.

Example 7

Stability of the Ghrelins in Aqueous Solution Having Various Kinds of pH Value (Test 1)

The stability of the ghrelins in aqueous solution with various kinds of pH value was conducted by using human ghrelin, which is one of the ghrelins.

Human ghrelin was dissolved in the purified water with about 0.03 μmol/mL (0.1 mg/mL). The pH of this solution was 4.7. This solution was divided into quarter, and one portion was kept alone and the pH values of the remaining three portions were adjusted to pH 1.8 (with 17 mM of hydrochloric acid), pH 3.9 (with 0.20 mM of hydrochloric acid) and pH 7.8 (with 0.24 mM of sodium hydroxide) respectively, by adding along with hydrochloric acid or sodium hydroxide aqueous solution.

These four solutions were stored at 25±2° C. for 1 and 3 day, and after storage, the HPLC analyses of each solutions were conducted to calculate the peak area ratio of human ghrelin, desacyl compound and Dha compound to the total peak area.

The results were summarized in the following Table 5.

TABLE 5

| | | Peak area ratio to total peak area (%) | | |
|---|---|---|---|---|
| | | Human ghrelin[a] | Desacyl compound[b] | Dha compound[b] |
| pH 1.8 | Before | 99.16 | 0.12 | 0.20 |
| | 1 day after | 97.68 | 1.46 | 0.31 |
| | 3 days after | 95.01 | 4.08 | 0.34 |
| pH 3.9 | Before | 99.21 | 0.07 | 0.20 |
| | 1 day after | 99.19 | 0.09 | 0.20 |
| | 3 days after | 99.14 | 0.14 | 0.19 |
| pH 4.7 | Before | 99.20 | 0.06 | 0.20 |
| | 1 day after | 99.12 | 0.15 | 0.21 |
| | 3 days after | 98.94 | 0.28 | 0.21 |
| pH 7.8 | Before | 98.85 | 0.33 | 0.24 |
| | 1 day after | 94.78 | 3.65 | 0.86 |
| | 3 days after | 87.84 | 9.84 | 1.65 |

[a]The place where ratio of peak area of human ghrelin is below 98% is under lined.
[b]The place where ratio of peak area of desacyl compound or Dha compound below 1% is under lined.

As shown in Table 5, more than 1% of the desacyl compound was produced in the aqueous solution of pH 1.8 and 7.8, and the ratio of human ghrelin was less than 98%, at only one day after storage. Further, the production ratio of Dha compound was more than 1% in the aqueous solution of pH 1.8 and 7.8 after 3 days' storage. On the contrary, the productions of the desacyl compound and Dha compound were inhibited in the aqueous solution of pH 3.9 and 4.7.

Accordingly, it was well understood that the aqueous solution having the pH range of 2 to 7 is suitable for inhibiting the production of the desacyl compound and the Dha compound. Therefore, it was confirmed that to obtain the stability of the ghrelins in, an aqueous solution, it was necessary to adjust the pH of the solution to 2 to 7 to prevent the various type of cleavage reactions at the hydrophobic group, which was the characteristic structure of the ghrelins.

Example 8

Stability of the Ghrelins in Aqueous Solution Having Various Kinds of pH Value (Test 2)

The stability of the ghrelins in aqueous solution with various kinds of pH value was conducted by using human ghrelin (1-7)amide, which is one of the ghrelins.

Human ghrelin(1-7)amide is common amino acid sequence of the ghrelins obtained from mammal, bird or fishes (cf. Table 1), and exhibits same biological activity as human ghrelin (International Patent Publication WO 01/07475).

Human ghrelin(1-7)amide was dissolved in the purified water with about 0.12 μmol/mL (0.1 mg/mL). The pH of this solution was 5.0. This solution was divided into quarter, and one portion was kept alone and the pH values of the remaining three portions were adjusted to pH 1.8 (with 17 mM of hydrochloric acid), pH 4.1 (with 0.05 mM of hydrochloric acid) and pH 7.9 (with 0.20 mM of sodium hydroxide) respectively, by adding with hydrochloric acid or sodium hydroxide aqueous solution.

These four solutions were stored at 25±2° C. for 1 and 3 day, and after storage, the HPLC analyses of each solutions were conducted to calculate the peak area ratio of human ghrelin(1-7)amide, desacyl human ghrelin(1-7)amide and [3-dehydroalanine]-human ghrelin(1-7)amide to the total peak area.

The results were summarized in the following Table 6.

TABLE 6

| | | Peak area ratio to total peak area (%) | | |
|---|---|---|---|---|
| | | Human ghrelin (1-7)amide[a] | Desacyl human ghrelin(1-7) amide[b] | [3-Dehydroalanine] human ghrelin (1-7)amide[b] |
| pH 1.8 | Before | 98.39 | 0.98 | 0.02 |
| | 1 day after | 95.40 | 3.75 | 0.07 |
| | 3 days after | 90.11 | 8.89 | 0.10 |
| pH 4.1 | Before | 98.76 | 0.72 | 0.00 |
| | 1 day after | 98.68 | 0.73 | 0.03 |
| | 3 days after | 98.60 | 0.77 | 0.01 |
| pH 5.0 | Before | 98.69 | 0.70 | 0.00 |
| | 1 day after | 98.57 | 0.73 | 0.02 |
| | 3 days after | 98.51 | 0.79 | 0.06 |
| pH 7.9 | Before | 98.22 | 1.12 | 0.03 |
| | 1 day after | 95.89 | 3.21 | 0.23 |
| | 3 days after | 92.54 | 6.21 | 0.54 |

[a]The place where ratio of peak area of human ghrelin (1-7)amide is below 98% is under lined.
[b]The place where ratio of peak area of human ghrelin (1-7)amide or [3-dehydroalanine]-human ghrelin(1-7)amide below 1% is under lined.

As shown in Table 6, the ratio of human ghrelin(1-7)amide was less than 98% in the aqueous solution of pH 1.8 and 7.9, at only one day after storage. On the contrary, the production of the degradation products was inhibited in the aqueous solution of pH 4.1 and 5.0.

Accordingly, it was well understood that the aqueous solution having the pH range of 2 to 7 was suitable for the aqueous solution containing human ghrelin(1-7)amide, which is one of the ghrelins. Therefore, it was confirmed that to obtain the stability of the ghrelins in an aqueous solution, it was necessary to adjust the pH of the solution to 2 to 7 to prevent the various type of cleavage reactions at the hydrophobic group, which was the characteristic structure of the ghrelins.

Example 9

Adsorption Inhibiting Effect of Anti-Adsorbents in Aqueous Solution Containing the Ghrelins with Low Concentration In the Example 6, it was shown that the ghrelins adhere to the wall of the vessel in the solution having medical applicable concentration of the ghrelins. Accordingly, the adsorption inhibiting effect of anti-adsorbents in aqueous solution containing the ghrelins was examined.

As the anti-adsorbent, the surfactant, that is, polyoxyethylene sorbitan monooleate (hereinafter, referred to as Tween® 80), and benzalkonium chloride were selected.

Human ghrelin was dissolved in 5% mannitol-0.05M glycine hydrochloride buffer solution (pH 3.5) with about 0.3 nmol/mL (1.0 μg/mL) concentration, which was the medical applicable concentration of the ghrelins. The anti-adsorbent was added to this solution with 0.01% or 0.1% concentration.

The human ghrelin concentrations of each solution were measured by HPLC method right after preparation, and these solutions were replaced in glass test tubes. After that, each solution were further replaced in new glass test tubes, and same operation was repeated for 5 and 10 times, then, the human ghrelin concentrations of each treated solution were measured by HPLC method. As a control, the solution not containing anti-adsorbent was examined.

Same procedure was repeated by using test tube made by polypropylene instead of glass test tube.

The results were summarizes in Table 7.

TABLE 7

| Anti-adsorbent | | Initial | Glass tube[a] | | Polypropylene tube[b] | |
|---|---|---|---|---|---|---|
| Species | Conc. | Conc. | 5 times | 10 times | 5 times | 10 times |
| None | — | 100 | 0 | 0 | 51 | 19 |
| Tween 80 | 0.01% | 100 | 17 | 0 | 90 | 90 |
|  | 0.1% | 100 | 20 | 5 | 93 | 91 |
| benzalkonium chloride | 0.01% | 100 | 81 | 64 | 97 | 96 |
|  | 0.1% | 100 | 99 | 99 | 99 | 101 |

[a]Asahi Techno-glass Co., Ltd.: 10 mL
[b]CORNING Co., Ltd.: 15 mL

As clearly shown in Table 7, the human ghrelin concentrations of the solutions were greatly reduced after the replacements of the solution in both cases using glass tubes and polypropylene tubes. Particularly, in the case of using glass tubes, the human ghrelin concentration of the solution was reduced to the level not detected by the HPLC analysis.

On the contrary, high adsorption inhibiting effect against polypropylene tube was observed when Tween® 80 was added to the solution with 0.01% or 0.1% concentration, as anti-adsorbent, and also high adsorption inhibiting effect against both glass tube and polypropylene tube was observed when benzalkonium chloride was added to the solution with 0.01% or 0.1% concentration, as anti-adsorbent.

Accordingly, it was well understood that Tween® 80 and benzalkonium chloride have a beneficial effect on inhibiting the ghrelins adsorption to the wall of the vessel, of the solution containing the ghrelins with the medical applicable concentration. Therefore, it was confirmed that the anti-adsorbent was effective to prevent the adsorption of the ghrelins during the manufacturing process, long-term storage and administering process.

Example 10

Adsorption Inhibiting Effect of Saccharides in Aqueous Solution Containing the Ghrelins with Low Concentration In the Example 9, it was shown that adsorption of the ghrelins to the wall of the vessel of the solution was inhibited by using anti-adsorbent. In this Example, the adsorption inhibiting effect of saccharides was examined.

As an aqueous solution of saccharide, 5% mannitol aqueous solution was used. Human ghrelin was dissolved in 5% mannitol aqueous solution with about 3 nmol/mL (10 μg/mL) and about 30 nmol/mL (100 μg/mL) concentration, which were the medical applicable concentration of the ghrelins. The The human ghrelin concentrations of each solution just prepared after were measured by HPLC method, and these solutions were replaced in polypropylene test tube. After that, each solution were further replaced in new polypropylene test tube, and same operation was repeated for 5 times totally, then, the human ghrelin concentrations of each treated solution were measured by HPLC method. As control, the physiological saline solutions containing human ghrelin with about 3 mmol/mL (10 μg/mL) and about 30 nmol/mL (100 μg/mL) concentration were examined.

The results were summarizes in Table 8.

TABLE 8

| | Anti-adsorbent | Initial | Polypropylene tube[b] |
|---|---|---|---|
| Species | Conc. of human ghrelin | Conc. | 5 times |
| Physiological saline | 10 μg/mL | 100 | 32 |
|  | 100 μg/mL | 100 | 89 |
| 5% mannitol aqueous solution | 10 μg/mL | 100 | 98 |
|  | 100 μg/mL | 100 | 99 |

[b]CORNING Co., Ltd.: 15 mL

As clearly shown in Table 8, the human ghrelin concentrations of physiological saline solutions were greatly reduced after the replacements of the solution by using polypropylene test tube. Particularly, the human ghrelin concentrations of the solution was reduced to 32% in the case of physiological saline solution containing human ghrelin with 10 μg/mL concentration.

On the contrary, high adsorption inhibiting effect against polypropylene tube was observed in the case of 5% mannitol aqueous solution containing human ghrelin with both 10 μg/mL and 100 μg/mL concentration.

Accordingly, it was well understood that saccharides showed a beneficial effect on inhibiting the ghrelins adsorption to the well of the vessel, in the solution containing the ghrelins with the medical applicable concentration, and therefore, it was confirmed that the saccharides were effective to prevent the adsorption of the ghrelins during the manufacturing process, long-term storage and administering process.

Example 11

Manufacture of the In Situ Preparation for Solution and its Stability

As the in situ preparation for the pharmaceutical composition of the present invention, lyophilized powder was prepared and the solubility of the powder was estimated.

Human ghrelin was dissolved in 5% mannitol-0.05M glycine hydrochloride buffer solution (pH 3.5) with about 0.3 nmol/mL (1.0 μg/mL) concentration, and the human ghrelin concentration of this solution just after preparation was measured by HPLC method, and pH value of this solution was also measured. As the results, the human ghrelin concentration was 1.0 μg/mL, and pH was 3.5. Then, this solution was lyophilized at −25° C. for 24 hours in vacuo, and the obtained powder was further dried at 20° C. for 24 hours in vacuo. The obtained lyophilized powder was white solid having good figure.

Then, this lyophilized powder was dissolved in the purified water, which amount was same as the decreased amount from the beginning of the lyophilization, and the solubility of the lyophilized powder and the pH of the obtained solution were examined.

As the result, the solubility of the lyophilized powder was excellent and no insoluble matter appeared in the solution, and the solubility of the powder was suitable for the in situ preparation for solution. The human ghrelin concentration was 1.0 μg/mL, which is same human ghrelin concentration of the solution just after the preparation or before the lyophilization, therefore, no decrease of content of the preparation by lyophilization was observed. Further, the pH value of the solution was 3.5, which was same pH value of the solution just after the preparation or before the lyophilization. Therefore, the aqueous solution stably containing human ghrelin can be obtained from the lyophilized powder of the present invention.

Accordingly, the lyophilized powder containing the ghrelins can be obtained by using the solution containing the ghrelins with adjustment of pH of the solution by lyophilization, and obtained lyophilized powder preparation is useful for the in situ preparation for the pharmaceutical composition of the present invention.

Manufacturing Example 1

Preparation of Pharmaceutical Composition Containing Human Ghrelin with pH Adjustment Human ghrelin, which is one of the ghrelins, was dissolved in purified water to obtain an aqueous solution containing human ghrelin with about 0.15 µmol/mL (0.5 mg/mL). The pH of this solution was adjusted to 4.0 by adding 0.1M hydrochloride acid solution, to obtain the pharmaceutical composition containing human ghrelin as the solution preparation.

Manufacturing Example 2

Preparation of Pharmaceutical Composition Containing Rat Ghrelin in Glycine Hydrochloride Buffer Solution Rat ghrelin, which is one of the ghrelins, was dissolved in 0.05M glycine hydrochloride buffer solution (pH 3.5) with about 0.15 µmol/mL (0.5 mg/mL) to obtain the pharmaceutical composition containing rat ghrelin as the solution preparation. The pH of this solution was 3.5.

Manufacturing Example 3

Preparation of Pharmaceutical Composition Containing [3-Serine(Acetyl)]Human Ghrelin in Glycine Hydrochloride Buffer Solution

[3-Serine(acetyl)]human ghrelin, which is one of the ghrelins, was dissolved in 0.05M glycine hydrochloride buffer solution (pH 3.5) with about 0.15 µmol/mL (0.1 mg/mL) to obtain the pharmaceutical composition containing [3-Serine (acetyl)]human ghrelin as the solution preparation. The pH of this solution was 3.5.

Manufacturing Example 4

Preparation of Pharmaceutical Composition Containing [3-Serine(Phenylpropionyl)]Human Ghrelin in Glycine Hydrochloride Buffer Solution

[3-Serine(phenylpropionyl)]human ghrelin, which is one of ghrelins, was dissolved in 0.05M glycine hydrochloride buffer solution (pH 3.5) with about 0.15 µmol/mL (0.5 mg/mL) to obtain the pharmaceutical composition containing [3-Serine(phenylpropionyl)]human ghrelin as the solution preparation. The pH of this solution was 3.5.

Manufacturing Example 3

Preparation of Pharmaceutical Composition Containing Human Ghrelin(1-5)Amide in Glycine Hydrochloride Buffer Solution Human ghrelin(1-5)amide, which is one of ghrelins, was dissolved in 0.05M glycine hydrochloride buffer solution (pH 3.5) with about 0.15 µmol/mL (0.5 mg/mL) to obtain the pharmaceutical composition containing human ghrelin(1-5) amide as the solution preparation. The pH of this solution was 3.5.

INDUSTRIAL APPLICABILITY

As described above, the present invention provides the pharmaceutical composition stably containing the ghrelins, and the preparation of the present invention prevents the adsorption of ghrelins to the wall of the vessel. Therefore, the present invention provides the pharmaceutical composition without decrease of the ghrelins, during the manufacture, long-term storage or administration.

The invention claimed is:

1. A method of improving the stability of ghrelin or its derivative in an aqueous solution comprising:
   adjusting the pH of the solution to be in the range of from 3 to 6;
wherein said aqueous solution is suitable for pharmaceutical administration to a human.

2. The method of claim 1, wherein the solution further comprises a pH adjuster or a buffer agent.

3. The method of claim 1, wherein the solution further comprises a pH adjuster comprising hydrochloric acid, sulfuric acid, nitric acid, boric acid, carbonic acid, bicarbonic acid, gluconic acid, sodium hydroxide, potassium hydroxide, aqueous ammonia, citric acid, monoethanolamine, lactic acid, acetic acid, succinic acid, fumaric acid, maleic acid, phosphoric acid, methanesulfonic acid, malic acid, propionic acid, trifluoroacetic acid, a salt thereof, or a mixture thereof.

4. The method of claim 2, wherein the solution further comprises a buffer agent comprising glycin, acetic acid, citric acid, boric acid, phthalic acid, phosphoric acid, succinic acid, lactic acid, tartaric acid, carbonic acid, hydrochloric acid, sodium hydroxide, a salt thereof, or a mixture thereof.

5. The method of claim 2, wherein the concentration of the pH adjuster or the buffer agent in the solution ranges from 0.01 mM to 1,000 mM.

6. The method of claim 1, wherein the solution comprises a buffer solution.

7. The method of claim 6, wherein the buffer solution comprises glycine hydrochloride buffer, acetate buffer, citrate buffer, lactate buffer, phosphate buffer, citric acid-phosphate buffer, phosphate-acetate-borate buffer, phthalate buffer, or a mixture thereof.

8. The method of 1, wherein the concentration of the ghrelin or its derivative in the solution ranges from 0.03 nmol/mL to 6 µmol/mL.

9. The method of claim 1, wherein the ghrelin or its derivative is in the form of an acetic acid salt.

10. The method of claim 1, wherein the ghrelin or its derivative comprises human ghrelin or its derivative.

11. The method of claim 1, wherein the pH of the solution is adjusted to be in the range of 4 to 5.

* * * * *